(12) United States Patent
Castro Lapetra et al.

(10) Patent No.: US 12,247,967 B2
(45) Date of Patent: Mar. 11, 2025

(54) METHOD FOR DETERMINING A FRESHNESS STATE OF A FOOD IN A STORAGE CONTAINER AS WELL AS COMPUTER PROGRAM PRODUCT AND STORAGE CONTAINER

(71) Applicant: BSH Hausgeraete GmbH, Munich (DE)

(72) Inventors: Cristina Castro Lapetra, Saragossa (ES); Regina De Diego Castilla, Guadalajara (ES); Daniel Garcia Romeo, Saragossa (ES); Sandra Ordovas Gracia, Muel (ES); Lander Rojo Esteban, Saragossa (ES)

(73) Assignee: BSH Hausgeraete GmbH, Munich (DE)

( * ) Notice: Subject to any disclaimer, the term of this patent is extended or adjusted under 35 U.S.C. 154(b) by 566 days.

(21) Appl. No.: 17/547,806

(22) Filed: Dec. 10, 2021

(65) Prior Publication Data

US 2022/0196623 A1    Jun. 23, 2022

(30) Foreign Application Priority Data

Dec. 17, 2020  (EP) ..................................... 20383116

(51) Int. Cl.
*G01N 33/00*  (2006.01)
*G01N 33/02*  (2006.01)

(52) U.S. Cl.
CPC ......... *G01N 33/02* (2013.01); *G01N 33/0036* (2013.01); *G01N 33/0062* (2013.01)

(58) Field of Classification Search
CPC ............... G01N 33/02; G01N 33/0036; G01N 33/0062; G01N 33/0024; G01N 33/025; G01N 33/03; G01N 33/04; G01N 33/0031; G01N 33/0075; G01N 33/0006; G01N 27/12; G01N 27/124; G01N 27/123; F25D 17/042; F25D 2700/06; F25D 2700/08; F25D 2700/123; F25D 29/00; G05B 23/0283; G06N 3/044; G06N 3/02; G06N 20/00; G06F 17/18; G06F 18/21; G06F 18/217; A23L 3/00
USPC ................ 62/125, 127, 129; 73/23.2, 29.01; 340/632, 539.22, 568.1, 540;
(Continued)

(56) References Cited

U.S. PATENT DOCUMENTS 8,455,798 B2 *  6/2013  Akdag ..................... F24C 7/085
219/413
11,674,940 B2 *  6/2023  Meyer ................ G01N 33/0016
73/23.2
(Continued)

FOREIGN PATENT DOCUMENTS

CN  109458785 A  *  3/2019  ........... F25D 29/008
DE  102005011304 A1 *  9/2006  ................ F24C 7/08
DE  102013214851 A1 *  2/2015  .............. F24C 7/085

*Primary Examiner* — Jeffrey P Aiello
(74) *Attorney, Agent, or Firm* — Laurence A. Greenberg; Werner H. Stemer; Ralph E. Locher

(57) ABSTRACT

A method based on sensor information of a MOX sensor. Sensor information captured at different operating temperatures in different freshness state determination cycles determines a freshness state of a food. Additional information relating to a food is determined. A storage container, a computer program product, and a household cooling appliance for carrying out the method.

16 Claims, 3 Drawing Sheets

(58) Field of Classification Search
USPC .......... 374/E1.003; 702/1, 188, 24, 187, 19, 702/130, 189, 184, 129, 127, 99, 81
See application file for complete search history.

(56) References Cited

U.S. PATENT DOCUMENTS

| | | |
|---|---|---|
| 2008/0008808 A1* | 1/2008 | Schonemann ............ F24C 7/08 426/523 |
| 2008/0159910 A1 | 7/2008 | Dick et al. |
| 2020/0200393 A1 | 6/2020 | Goldberg et al. |
| 2020/0333310 A1 | 10/2020 | Lee et al. |
| 2021/0190747 A1* | 6/2021 | Cobley .............. G01N 33/0022 |
| 2021/0382026 A1* | 12/2021 | Narula ................... G01N 21/03 |

* cited by examiner

METHOD FOR DETERMINING A FRESHNESS STATE OF A FOOD IN A STORAGE CONTAINER AS WELL AS COMPUTER PROGRAM PRODUCT AND STORAGE CONTAINER

CROSS-REFERENCE TO RELATED APPLICATION

This application claims the priority, under 35 U.S.C. § 119, of European Patent Application EP 20383116.9, filed Dec. 17, 2020; the prior application is herewith incorporated by reference in its entirety.

FIELD AND BACKGROUND OF THE INVENTION

One aspect of the invention relates to a method, in particular a computer-implemented method, for determining a freshness state of a food in a storage container. A further aspect of the invention relates to a computer program product. Moreover, one aspect of the invention relates to a storage container for food.

From the prior art it is known that food is stored in storage containers. Such storage containers are commonly arranged in a household cooling appliance. In particular therein they may be arranged in a cooling compartment of the household cooling appliance. A storage container may for instance comprise a bowl. Moreover, also storage containers are known which additionally comprise a cover so that the bowl is closed.

However, it is also known that food stored in such storage containers changes its freshness state. This applies both to vegetables as well as to fruits. Moreover, however, this also applies to meat. In this context, due to the most varied criteria the freshness state of a food can be changed in such a way that consumption is no longer possible or no longer advisable. Such scenarios commonly result in that the food is disposed of in the garbage. Thereby also a considerable waste of food is caused.

It is also known that there are possibilities to observe the freshness state of a food. However, here merely systems are known that allow for an only very rudimentary determining of such freshness state. Thereby the determination is very inaccurate. For instance sensors may be employed here, which determine the concentration of a molecular compound in a gas. Based on this concentration then a statement about the freshness state is to be made.

It is also known that MOX (metal-oxide) sensors are employed for the analysis of gas. However, here only embodiments are known in which a specific operating temperature of this MOX sensor can be set and then a specific sensitivity of this sensor occurs so that the sensor, however, is more sensitive to a specific molecular compound than to others.

SUMMARY OF THE INVENTION

It is the object of the present invention to provide a method, a storage container, a computer program product, and a food keep-fresh system, in which the freshness state of a food can be monitored in an improved manner.

This object is solved by a method, a storage container, a computer program product, and a food keep-fresh system according to the independent claims.

One aspect of the invention relates to a method, in particular a computer-implemented method, for determining a freshness state of a food in a storage container, the method comprising the following steps:

performing a first freshness state determination cycle of the food by, setting a first operating temperature of at least one MOX sensor, and capturing a gas mixture in the storage container by the MOX sensor at the first operating temperature;

setting at least one second operating temperature of the MOX sensor that is different from the first operating temperature, and capturing a gas mixture in the storage container by the MOX sensor at the second operating temperature;

determining, by an evaluation unit, a state of the gas mixture based on the information captured at the at least two operating temperatures during the first freshness state determination cycle;

performing a second freshness state determination cycle of the food temporally consecutively to the first freshness state determination cycle, in the second freshness state determination cycle, setting the first operating temperature of the MOX sensor, and capturing a gas mixture in the storage container by the MOX sensor at this first operating temperature;

setting at least the second operating temperature of the MOX sensor that is different from the first operating temperature, and capturing a gas mixture in the storage container by the MOX sensor at the second operating temperature;

determining, by the evaluation unit, a state of the gas mixture based on the information captured at the two operating temperatures during the second freshness state determination cycle;

determining, by the evaluation unit, the freshness state of the food in the storage container based on the state of the gas mixture that was determined in the first freshness state determination cycle and based on the state of the gas mixture which was determined in the at least second freshness state determination cycle.

By the method an electronic information is generated which characterizes the freshness state of the food. The gas mixture in the storage container characterizes the food in its respective freshness state. Therefore, the detection and analysis of the gas mixture and not only of one individual molecule of a gas is very advantageous, in particular since the composition of the gas mixture characterizing the respective freshness state may change if the freshness state changes. Therefore, a gas mixture detection and its analysis are very advantageous. By the suggested new operating mode of a MOX sensor the statement about the freshness state of the food is more precise. In a measurement cycle by this new operating mode of the MOX sensor an analysis of substantially the entire gas mixture also with regard to several molecular components is possible. By the change in temperature of the MOX sensor, the same can be substantially improved in terms of its selectivity and sensitivity. Since various molecules are detected only at different temperatures, the temperature-varying operating mode of the MOX sensor is particularly advantageous. Moreover, by performing at least two separate measurement cycles or freshness state determination cycles the temporal change in the freshness state can be recognized even more precisely, in particular by the respective analysis of the respective gas mixture.

A further independent aspect of the invention relates to a method, in particular a computer-implemented method for determining a freshness state of a food in a storage container, in particular for determining an electronic information relating to a freshness state of a food in a storage container, the method comprising the following steps:

providing a captured information relating to a gas mixture in a storage container, in which the food is located, wherein the captured information is captured at a set first operating temperature of a MOX sensor in a first freshness state determination cycle, to an evaluation unit;

providing a captured information relating to a gas mixture in the storage container, in which the food is located, wherein the captured information is captured at a set second operating temperature of the MOX sensor in a first freshness state determination cycle, to the evaluation unit;

determining a state of the gas mixture depending on the information captured at the two operating temperatures in the first freshness state determination cycle by the evaluation unit;

providing a captured information relating to a gas mixture in the storage container, in which the food is located, wherein the captured information is captured at a set first operating temperature of the MOX sensor in a second freshness state determination cycle, to the evaluation unit;

providing a captured information relating to a gas mixture in the storage container, in which the food is located, wherein the captured information is captured at a set second operating temperature of the MOX sensor in the second freshness state determination cycle, to the evaluation unit;

determining a state of the gas mixture depending on the information captured at the two operating temperatures in the second freshness state determination cycle by the evaluation unit;

determining the freshness state of the food in the storage container depending on the state of the gas mixture which was determined in the first freshness state determination cycle and depending on the state of the gas mixture which was determined in the at least second freshness state determination cycle by the evaluation unit.

By the method based on several pieces of captured electronic information the freshness state can be determined fast and precisely by the evaluation unit. The captured information is in particular received by the evaluation unit. With regard to the providing consequently in particular a receiving is effected by the evaluation unit.

In an embodiment in the first freshness state determination cycle at least at one, in particular at all of the operating temperatures of the MOX sensor at least at two different points in time a capturing of the at least one characteristic feature of the gas mixture is performed, and/or in the second freshness state determination cycle at least at one, in particular at all of the operating temperatures of the MOX sensor at least at two different points in time a capturing of the at least one characteristic feature of the gas mixture is performed. Thereby the data base is rendered more comprehensive and more precise.

In an embodiment at least one operating temperature is set in at least one of the freshness state determination cycles for a period of time of between 150 ms and 250 ms, in particular between 190 ms and 210 ms. By such a short time interval, on the one hand, the performing of at least one measurement, in particular of a number of measurements, larger than or equal to 1 and smaller than or equal to 5 can be performed. On the other hand, thereby the time interval is short enough for the several operating temperatures of the MOX sensor to be set and then measurements to be effected. Thereby also the entire time period of a freshness state determination cycle is kept relatively short.

In particular, the period of time for an entire freshness state determination cycle is less than 15 s, in particular less than or equal to 10 s.

In an embodiment as a state of the gas mixture in the freshness state determination cycles a molecular composition of the gas mixture at the respective points in time at which the operating temperatures were set is determined and/or as a state of the gas mixture in the freshness state determination cycles a change in the molecular composition of the gas mixture from one freshness state determination cycle to another freshness state determination cycle is determined. This very analysis facilitates very accurately a statement about the respective freshness state of the food.

In an embodiment as captured information actual signal sequences of the MOX sensor are considered, which are compared with reference signal sequences. Depending on the comparisons the states of the gas mixture are determined and depending thereon then the freshness state of the food is determined. In particular, here, signal sequences of the electrical resistance of the MOX sensor are taken into consideration. In an embodiment a reference signal sequence is a temporally contiguous signal sequence. In particular, a reference signal sequence characterizes a temporal sequence of the freshness state of a food in the storage container for a period of time of the food in the storage container. In particular, this period of time starts with the point in time of placing the food into the storage container. In particular, this period of time ends with the freshness state of the food, at which the food has gone off. Thereby, in an embodiment an advantageous reference signal sequence characterizes the entire spectrum of a freshness state and its change of a specific food. Thereby very comprehensive comparisons with the actual signal sequences can be performed. This is because then also actual signal sequences can be compared with only a part of a reference signal sequence. Thereby very exact determinations of a current freshness state can be executed. Equally, it is thereby also facilitated to make more accurate predictions as to when and how the current freshness state of the food will change. This is because if the actual signal sequence coincides or nearly coincides with a portion of a reference signal sequence, it can also be exactly predicted how the actual signal sequence will result in the future, namely similar or identical to the reference signal sequence. Thereby it can also be predicted more accurately how and when the current freshness state of the food will change.

A reference signal sequence in an embodiment, however, may also characterize only a portion of the entire spectrum of a temporal sequence of a freshness state of a food in a storage container.

The reference signal sequences can be determined by machine training of a food keep-fresh system. Thereby comprehensively very many freshness states of many kinds of food can be exactly determined. The possibility of being able to provide very many and accurate reference signal sequences and to always continuously update and improve them is thereby given.

The reference signal sequences are preferably determined in preprocessing phases. They can then be saved in a memory of the food keep-fresh system.

In an embodiment by the reference signal sequences specific freshness states of the food are characterized.

In an embodiment by the reference signal sequences freshness state classes of the food are defined. Depending on the comparing of the actual signal sequences with the reference signal sequences the current freshness state of a food is classified into a freshness state class by the evaluation unit.

In an embodiment at least two freshness state classes are predetermined. By a first freshness state class in particular a freshness state is specified, in which the food is free of mold. By a second freshness state class in an embodiment a freshness state is specified in which the food already has developed, in particular, has just started to develop mold.

In an embodiment in the determining of the freshness state a probability is determined by the evaluation unit, by which the assignment of the determined freshness state with a freshness state class is characterized.

In an embodiment the reference signal sequences are machine trained in a preprocessing phase of the method.

In an embodiment the determining of the freshness state of the food item in the storage container is at least proportionately performed by machine training.

The machine training facilitates an even better analysis and a system that grows even more intelligent over the period of time. The classification allows for a very sophisticated evaluation of the freshness state. By the classes a more individual and more structured assignment of the freshness states can be effected.

In an embodiment the determined freshness state of the food is output on an output unit. In particular, the output unit may be an optical display unit. In particular, a color representation is effected, which optically symbolizes the freshness state. For instance here three colors, for instance green, yellow, and red may be predetermined. Green may characterize an absolutely fresh state. Yellow may characterize an in this regard deteriorated state of the food, which, however, is still fully suitable for consumption. Red may characterize a putrid state. In particular, the output unit can be an acoustic unit to symbolize the state of freshness. The sounds can be expressions or texts or in any language or be different sounds associated with different states of freshness. The output unit can also be a display of a smart device and where the state of freshness is shown visually or audibly on it.

In an embodiment when performing a freshness state determination cycle a temperature profile is predetermined for the determination temperature a temperature profile, which is an ascending and/or descending stepped profile, so that temporally consecutively in the case of more than two operating temperatures the gas mixture is captured at least once in each case by the MOX sensor.

In an embodiment, the freshness state determination cycles are performed immediately following one another without capturing pause. In another embodiment a capturing pause between the at least two freshness state determination cycles is performed. This may be several minutes or several hours long.

Generally, it may be envisaged that the food is captured by a detector, which is different from a MOX sensor. For instance, the detector may be a camera. Thereby for instance at the onset of a loading of the storage container with storage goods or food it is identified what kind of food is stored. Equally it is also possible that a user inputs into an input unit which food is or was stored in the storage container. Such an input unit may also be a touch-sensitive operating device. This may be integral part of a display. The display may for instance be arranged on the storage container. But it may also be arranged on a front side of a door of a household cooling appliance. Based on this information the evaluation unit can evaluate the information of the MOX sensor even more precisely. Since different kinds of food at least partially produce different gases in the case of a change in freshness and/or in different phases of the change in freshness respective different gases, by this way of proceeding the determination can be effected even more accurately for a specific food. In particular, thus, also freshness states for several different kinds of food, which are stored together in a storage container, can be analyzed even more individually and precisely.

In particular, an electronic food keep-fresh system may be envisaged. This can execute the above-named method. It may comprise at least one evaluation unit. This evaluation unit may be arranged in a household cooling appliance. The evaluation unit, however, may also be arranged external to the household cooling appliance and configured for communication with the household cooling appliance. To this end, emitting and/or receiving units may be provided. The food keep-fresh system may be integral part of a communication network. With this may also be associated several household appliances. The communication network may also comprise a backend. Thereon evaluations and/or data, in particular, also relating to the freshness states of other food and/or in other storage containers, can be gathered. The data can also be evaluated on the backend. These data can then be provided to food keep-fresh systems. Thereby an analysis of a food keep-fresh system with regard to a freshness state of a food item in a storage container can be rendered more accurate.

A further independent aspect of the invention relates to a method, in particular a computer-implemented method, for determining a statement relating to a stored food. A further independent aspect relates to a method, in particular a computer-implemented method, for operating a food keep-fresh system, the method comprising the following steps are performed:

providing an electronic information relating to a freshness state of a food in a storage container to an evaluation unit;

generating at least one electronic future information relating to the food depending on the provided electronic information by the evaluation unit;

providing the generated electronic future information by the evaluation unit; and outputting the electronic future information at an output unit.

By such a method it is facilitated to allow for future planning and ways of acting starting from a current freshness state of a food in a more specific way. Thus, it can be prevented more reliably that food grows stale and can no longer be consumed. Thus, the waste of food can be reduced. By this future information generated on the part of the system in particular a user can also currently better understand what bearings the current freshness state has in the future and/or which options the user, in particular which future time intervals, he has to be able to use the food.

The current freshness state of the food in an embodiment can be determined by a method according to the above-named aspect or an advantageous embodiment thereof.

In an embodiment as an electronic additional information a consumption sequence is generated, in which food in the storage container is to be consumed.

In an embodiment as an electronic additional information a prediction information is generated in which the future freshness state and/or the future change in the freshness state are estimated.

In an embodiment as an electronic additional information a storage information is generated, by which storage conditions for the food are suggested for the future.

In an embodiment as an electronic additional information a reminder information is generated, by which a reminder is generated that the food is stored in the storage container.

In an embodiment as an electronic additional information a preparation information is generated, by which a preparation suggestion for a consumption of the food is suggested.

In an embodiment the electronic future information is output at an output unit of a portable mobile radio terminal device.

In an embodiment for determining the future information also a humidity and/or a temperature in the storage container may be considered. This may be in each case values from the past and/or current values.

In an embodiment the electronic future information is output at an output unit of a household cooling appliance. In an embodiment the electronic future information is output at a display of a household cooling appliance. The display may be arranged on a front side of a door of the household cooling appliance.

In an embodiment in addition to the electronic future information the freshness state is output as information by the output unit.

One further independent aspect of the invention relates to a food keep-fresh system with an evaluation unit, wherein the food keep-fresh system is configured for performing a method according to an above-named aspect or an advantageous embodiment thereof. In particular, the method is performed by the food keep-fresh system.

In an embodiment the food keep-fresh system comprises a storage container for food, which comprises a storage bowl intentionally configured for storing food. The food keep-fresh system moreover comprises at least one MOX sensor.

In an embodiment the food keep-fresh system comprises a backend, on which the information relating to the freshness state is deposited. On this backend also a lot of information relating to the freshness state may be deposited. This may relate to different foods. It is also possible that freshness states of identical items of food, which are deposited in separate storage containers and/or in separate household cooling appliances, are deposited. Thereby it is also facilitated that for the determination of the freshness state of a food and/or for the determination of at least one electronic future information this plural information of freshness states can be taken into consideration. Equally, in an embodiment thereby also a learning system is facilitated, if it is recognized and/or captured and/or notified, whether and/or when and/or how the at least one electronic future information was used and/or implemented. Thereby the system in a self-learning manner can also draw conclusions as to how suitable an electronic future information was.

A further aspect relates to a computer program product, comprising instructions, which, when executing the program by a computer, cause the same to perform a method according to a named independent aspect or an advantageous embodiment thereof.

A further aspect of the invention relates to a storage container for food, comprising a storage bowl, which intentionally is configured for storing food, comprising at least one MOX sensor, and comprising an evaluation unit, wherein the storage container is configured for performing a method according to a named independent aspect or an advantageous embodiment thereof. In particular, the method is performed by the storage container.

A further independent aspect of the invention relates to a computer-readable storage medium, comprising instructions, which, when executed by a computer, cause the same to perform a method according to a named independent aspect or an advantageous embodiment thereof.

Generally, embodiments of an independent aspect are to be regarded as advantageous embodiments of another independent aspect.

Further features of the invention are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by the separated feature combinations from the explained implementations. Implementations and feature combinations are also to be considered as disclosed, which thus do not comprise all of the features of an originally formulated independent claim. Moreover, implementations and feature combinations are to be considered as disclosed, in particular, by the implementations set out above, which extend beyond or deviate from the feature combinations set out in the back-references of the claims.

Other features which are considered as characteristic for the invention are set forth in the appended claims.

Although the invention is illustrated and described herein as embodied in method for determining a freshness state of a food in a storage container as well as computer program product and storage container, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

In the figures the same elements and elements having the same function are equipped with the same reference signs.

Figure 1:
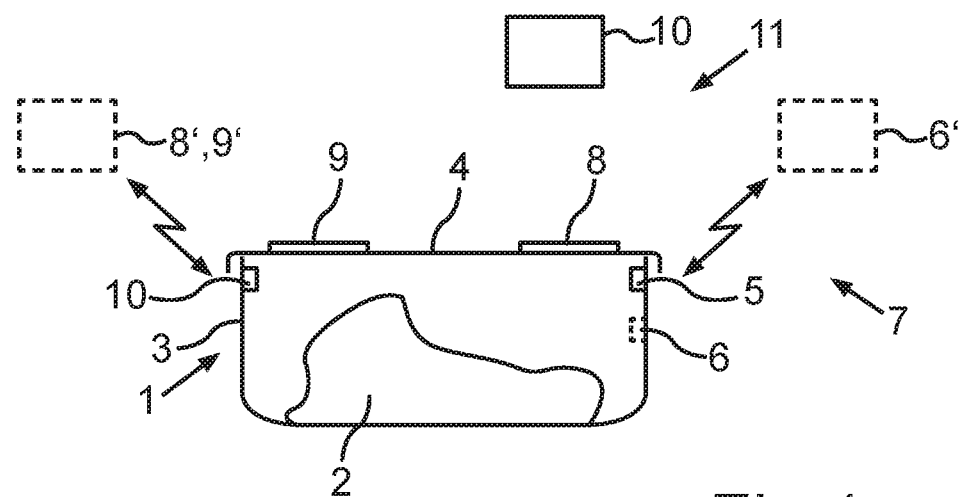
FIG. 1 a schematic view of an embodiment of a storage container according to the invention.

In FIG. 1 in a schematic representation an embodiment of a storage container 1 is shown. The storage container 1 is intentionally configured for storing at least one item of food 2. The storage container 1 comprises a storage bowl 3. In an embodiment the storage container 1 moreover also comprises a cover 4. In the embodiment this is arranged on the storage bowl 3 for closing the same. The storage container 1 may be closed. In this regard it may also be closed in a gas-proof manner. In another embodiment the closed state is configured to be also gas-permeable. In this context, for instance, the interface between the cover 4 and the bowl 3 may be configured to be gas-permeable. Additionally, or instead, ventilation openings may be formed in the storage bowl 3 and/or the cover 4.

The storage container 1 in an embodiment may also be configured as keep-fresh container. Thereby in the interior of the storage container 1 storage conditions may be set which are defined differently from the storage conditions in a receiving space for food of the household cooling appliance. Thus, the corresponding storage container 1 can be placed into such receiving space of a household cooling appliance and the food 2 stored therein can be stored under storage conditions that are different from the storage conditions of the food in the remaining receiving space of the household cooling appliance.

The storage container 1 in the embodiment comprises at least one MOX sensor 5. Neither the number nor the position are to be taken in a limiting way in FIG. 1. The MOX sensor may also be arranged on the cover 4, if such is present.

In an embodiment the storage container 1 also comprises an electronic evaluation unit 6. The electronic evaluation unit 6 may, for instance, be arranged on the storage bowl 3.

In an embodiment a food keep-fresh system 7 is provided. This may comprise the storage container 1. This may be correspondingly designed, as it has been explained in the above-named embodiments. The food keep-fresh system 7 may additionally or instead of the evaluation unit 6 comprise an evaluation unit 6', which then is arranged external to the storage container 1. For instance then a wireless communication between the evaluation unit 6' and the storage container 1, in particular the MOX sensor 5, is effected.

In the named embodiments the storage container 1 in an embodiment may also comprise an output unit 8. This may be an optical and/or acoustic output unit 8. Thereby information can be output optically and/or acoustically. The output unit 8 may for instance be arranged on the cover 4. However, it may also be arranged for instance on the storage bowl 3.

In a further embodiment the storage container 1 comprises an input unit 9. The input unit 9 may be configured for manual and/or acoustic input of information by the user.

The input unit 9 may be arranged on the cover 4. However, it may also be arranged on the storage bowl 3.

In an embodiment the storage container 1 also comprises at least one optical capturing unit 10. The optical capturing unit 10 may for instance be a camera. It may be arranged on the cover 4 or on the storage bowl 3. By this optical capturing unit 10 the storage container 1 itself or the food keep-fresh unit 7 itself can recognize, which food 2 is arranged in the storage container 3. Thus, a primary information can be optically captured. This primary information can then be provided to the evaluation unit 6 or 6'.

In an embodiment the display unit 8 may also be configured as external display unit 8' and/or be present in addition thereto. Equally, for instance also the input unit 9 may be configured as input unit 9' external to the storage container 1 and/or be provided in addition thereto. Here, too, then in an embodiment in each case a wireless communication with the storage container 1, in particular also the evaluation unit 6 may be effected.

In a further embodiment the storage container 1 may also be an integral part of a communication network 11. The communication network 11 may be a domestic network. By this communication network 11 several household appliances may be wirelessly networked. In this regard they may be directly interlinked. In an embodiment this communication network 11 may also comprise a backend 12. Thereon information may be deposited, in particular also centrally. For instance correspondingly deposited information can be provided to the evaluation unit 6 or 6'. In the backend 12 for instance information about the freshness states of various kinds of food can be deposited. They may be from one storage container 1. They may, however, also be from various storage containers 1 and/or various household cooling appliances. Thus, information about freshness states and/or electronic future information relating to a single item of food or to several different items of food may be deposited.

The food keep-fresh system 7 also comprises a computer program product. This computer program product comprises instructions, which upon execution of the program by a computer cause the same to perform a method for determining a freshness state of a food 2 in a storage container 1.

This computer program product may for instance be deposited on the evaluation unit 6 or the evaluation unit 6'. The computer program product, however, may also be deposited in the backend 12.

Figure 2:
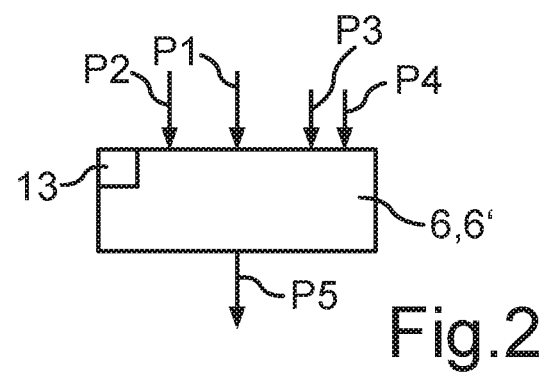
FIG. 2 a schematic view of an evaluation unit, by which in an embodiment a method for determining a freshness state of a food is performed.

In FIG. 2, to this end, a schematic representation of an evaluation unit 6 or 6', respectively, is shown. The evaluation unit 6 or &comprises a computer program product 13, here represented symbolically.

For instance, to be able to determine the freshness state of the food 2 in the storage container 1 by a computer-implemented method, to start with, the providing of a captured information relating to the gas mixture in the storage container 1, in which the food 2 is located, is performed according to the arrow P1. This first information was captured in a first freshness state determination cycle by the MOX sensor 5. This MOX sensor 5, for this purpose, was operated in a defined way at a set first operating temperature, at which a corresponding measurement for capturing this first information has been done. In particular, this first electronic information is received by the evaluation unit 6 or 6', respectively.

Moreover, according to the arrow P2 a providing of a captured information relating to a gas mixture in the storage container 1, in which the food 2 is located, is effected. This captured information was captured by the MOX sensor 5 in this first freshness state determination cycle. This was effected in a defined way by the MOX sensor at a set second operating temperature, which is different from the set first operating temperature. This second electronic information is received by the evaluation unit 6 or 6', respectively.

By the evaluation unit 6 or 6', respectively, then a determining of a state of the gas mixture in the storage container 1 is effected depending on these two pieces of information captured in the first freshness state determination cycle.

In an embodiment moreover then a providing of a further captured information relating to the gas mixture in the storage container 1 is effected, in which the food 2 is located, which in FIG. 2 is symbolized by the arrow P3. This further captured information was captured by the MOX sensor 5 in a second freshness state determination cycle following the first freshness state determination cycle. In particular therein a first operating temperature of the MOX sensor 5 was set. This first captured electronic information is received by the evaluation unit 6 or 6', respectively.

According to a further way of proceeding, a providing of a captured information relating to the gas mixture in the storage container 1, in which the food 2 is located, is effected. This further captured information was captured by the MOX sensor 5 in this second freshness state determination cycle. It was captured at a second operating temperature, which here, too, was set in a defined way and is different from the first operating temperature. It is symbolized by the arrow P4. This second captured electronic information is received by the evaluation unit 6 or 6', respectively. Then also again a determining of a state of the gas mixture is effected depending on the information captured at the two operating temperatures in the second freshness state determination cycle.

In a further step by the evaluation unit 6 or 6', respectively, a determining of the current freshness state of the food 2 in the storage container 1 is performed. This is effected depending on the state of the gas mixture determined in the first freshness state determination cycle. It also is effected depending on the state of the gas mixture determined in the at least second freshness state determination cycle. By the evaluation unit 6 or 6', respectively, then an information P5 can be provided, which characterizes this determined freshness state of the food.

This means that thus, to start with, a method is provided as computer-implemented method, in which specific information is provided to the evaluation unit 6 or 6', respectively, the same depending on this provided captured information determines the freshness state of the food 2 and provides this determined information relating to the freshness state.

In an embodiment in this context, it is envisaged with regard to the method that, to start with, the food 2 is placed into the storage container 1. Then a first freshness state determination cycle of the food 2 is performed. To this end, a first operating temperature of at least the one MOX sensor 5 is set in a defined way. At this first operating temperature a gas mixture is captured in the storage container 1 by this MOX sensor 5.

In a temporally consecutive step then at least one second operating temperature of the MOX sensor 5 that is different from the first one is set in a defined way. At this second operating temperature the gas mixture in the storage container 1 is captured by the MOX sensor 5. This equally is effected during the continuing first freshness state determination cycle.

After finishing the first freshness state determination cycle at least one second freshness state determination cycle for the food 2 is performed. The at least one second freshness state determination cycle can be performed immediately temporally consecutively to the first freshness state determination cycle. However, in an embodiment it may also be envisaged that between the at least two freshness state determination cycles there is a pause. This may last several minutes or several hours.

In an embodiment many freshness state determination cycles for determining a freshness state of the food 2 are performed. In this regard a plurality of immediately consecutive freshness state determination cycles are performed. Thereby a continuous capturing of the respective current freshness state can be effected.

In an embodiment per freshness state determination cycle more than two different operating temperatures of the MOX sensor 5 are set in a defined way and in each case at least a one-time capturing of the gas mixture during such a set operating temperature is performed. Preferably, however, per set operating temperature of a MOX sensor several, in particular in each case several, capturing processes of the gas mixture are performed by the MOX sensor. In particular two, in particular in each case three, such capturing processes per set operating temperature are performed. It may be envisaged in an embodiment that these different measuring processes per operating temperature in each case are performed at equal time intervals relative to each other.

In an embodiment an operating temperature of a MOX sensor is set in a defined way and also for a certain period of time set in a defined way. This period of time may amount to between 150 ms and 250 ms, in particular between 190 ms and 210 ms. In the case of such time interval then in an embodiment it may be envisaged that a first capturing process of the MOX sensor is performed at the onset of this set operating temperature. A second capturing process may then be performed at this set operating temperature approximately halfway through the period of time for which this operating temperature is set. In an embodiment a third capturing process may be performed at the end of this time interval for which this operating temperature of the MOX sensor is set.

In the case of the at least one further freshness state determination cycle of the food 2 again the setting of a first operating temperature of the MOX sensor 5 follows. Then the gas mixture in the storage container 1 is captured by the MOX sensor 5 at least once. Subsequently, then during the same, at least one second freshness state determination cycle a second operating temperature of the MOX sensor 5 that is different from the first one is set. Then at this set second operating temperature at least once the gas mixture in the storage container 1 is captured by the MOX sensor.

The first operating temperature may be the same in the performed freshness state determination cycles. The at least second operating temperature may be the same in the performed freshness state determination cycles.

Depending on this information then, on the one hand, the states of the gas mixture are determined by the evaluation unit 6, 6' for the respective performed freshness state determination cycles depending on the information captured at the respective operating temperatures. Depending thereon, as already set out with regard to FIG. 2 in the above, the freshness state of the food 2 in the storage container 1 is determined. This determined freshness state is provided by the evaluation unit 6, 6' in particular as electronic information.

Depending on the determined result of the freshness state of the food 2 in an embodiment a symbolic representation on the output unit 8 or 8', respectively, may be effected. For instance here, a color characterization of the determined freshness state may be effected. It may for instance be envisaged that a green representation is effected if the freshness state is unimpaired. This means that the consumability of the food 2 is unquestionable. If the freshness state in this regard has progressed, in an embodiment a yellow color representation on the display unit 8 or 8', respectively, may occur. If the freshness state for instance is already relatively poor and consumption of the food 2 no longer possible without reservations, an optical representation by the color red on the output unit 8 or 8', respectively, may be provided.

In an embodiment as a state of the gas mixture in the freshness state determination cycles a composition of the gas mixture at the respective points in time at which the operating temperatures were set is determined. Additionally, or instead, a state of the gas mixture in these freshness state determination cycles may be a change of the composition of the gas mixture of a freshness state determination cycle in another freshness state determination cycle. This, too, may be determined accordingly.

In an embodiment it is for instance also possible that as captured information actual signal sequences of the MOX sensor 5 are considered. This is a further very advantageous embodiment. This is because thus no explicit capturing of concentrations of molecules of the gas mixture needs to be performed. By comparing these captured actual signal sequences with saved reference signal sequences the states of the gas mixture can be determined.

In an embodiment such reference signal sequences can be determined multiply in preprocessing phases and also development phases of the storage container 1. Thus, reference signal sequences for different kinds of food can be determined. Thereby for one or several kinds of food also very precisely their respective freshness state and/or a change in the freshness state can be analyzed. Thus, manifold and very precise reference signal sequences can be determined. For instance, in this context, also a machine training can be performed. In this machine learning a preprocessing and a classification of the freshness states may occur. By the reference signal sequences thus manifold specific freshness states of a food or of several kinds of food are characterized. By the machine training and classifying this can be effected, on the one hand, very simply and, on the other hand, also very comprehensively.

Depending on these comparisons between the actual signal sequences and the reference signal sequences the states of the gas mixture can be determined and depending thereon the freshness state of the food be determined.

In an embodiment these reference signal sequences can be saved in the evaluation unit 6 or 6', respectively, and/or in the backend 12.

However, it is also possible that such a machine training is effected not only in such a preprocessing phase. Rather, then also during the actual operation of such system such machine learning can be performed.

It is also common that based on these approaches a classification is predetermined. Depending on the represented analyses and determinations then a classification of the food 2 into a freshness state class can be effected. For instance, it may be envisaged that at least two different freshness state classes are predetermined. One of these freshness state classes may specify a freshness state, in which the food 2 is still free of mold. By a second freshness state class a freshness state can be specified in which the food already has developed, in particular, has just started to develop mold. Also, the classifying can be machine trained.

In a further embodiment it may be envisaged that when determining the freshness state also a probability is determined by the evaluation unit 6 or 6', respectively. By this probability an assignment of the determined freshness state to a freshness state class can be characterized. Thus, the respective ways of proceeding for determining a freshness state can be effected in a more specific and more variable way and thus also more in line with demand and more precisely. Thus, in the very case of a classification and the advantageously indicated probability value a further information can be provided. Thus, the classification can be still better individually assessed.

In the case of food that is stored due to the storage conditions such as storage time and/or humidity and/or storage temperature different processes in changes in the freshness state of the food occur. Invariably involved are characteristic molecules which are generated and/or proliferate in the process. Thus, by the suggested method it is facilitated very advantageously that it is not required to detect molecules in their concentration, but rather that quasi the gas mixture as such is comprehensively analyzed, this means the presence of molecules during certain phases.

With many kinds of food in the case of a change in the freshness state, in particular a deterioration of the freshness state, an occurrence of VOC (Volatile Organic Compounds) is involved. These are thus also characteristic of the respective freshness states and changes in freshness states. In particular, ester compounds are to be named as dominant molecules. Moreover, also ethylene compounds or ethyl acetate compounds are known in such gas mixtures.

With regard to the above-named classification of freshness states a normalization of a general analysis of components can be performed by classifiers. As classifiers here for instance MLP (Multilayer Perceptron) or GBD (Gradient Boosting Decision Tree) or a logistic regression or the like can be used. As classifiers therein is to be understood a hypothesis about a discrete value function, which is used to assign a class identification to specific data points. By the exemplarily named classifiers in this regard examples of such hypotheses are indicated. Thus, also an unambiguous relationship between the sensor information and the defined classes can be generated. Thus, also an unambiguous association of actual signal sequences with freshness state classes is facilitated. This is the case via the above-mentioned possibility of comparing the actual signal sequences with the reference signal sequences.

Particularly advantageous is the analysis by the dynamic operating mode of the MOX sensor. Dynamic, in this context, means that the MOX sensor is operated at least at two different operating temperatures and at each of these operating temperatures capturing or measuring operations of characteristic criteria of the gas mixture are performed.

Figure 4:
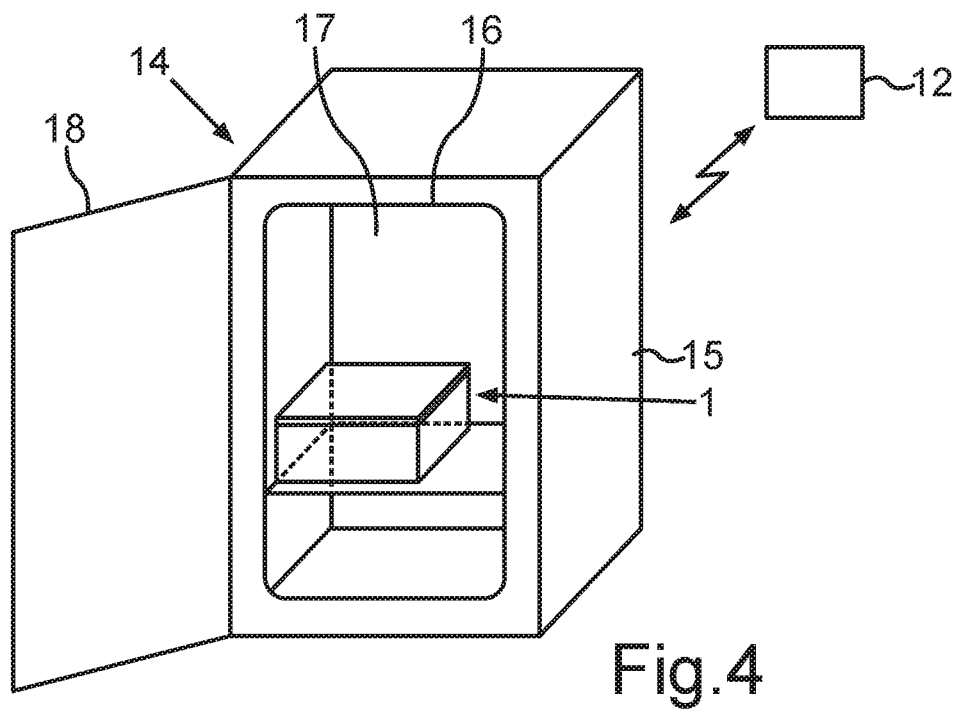
FIG. 4 a schematic view of an embodiment of a household cooling appliance according to the invention.

In FIG. 4 an embodiment of a household cooling appliance 14 is shown. The household cooling appliance 14 is configured for storage and preservation of food. The household cooling appliance 14 may be a cooling appliance or a freezer or a fridge-freezer combination appliance. The household cooling appliance 14 comprises a housing 15. In the housing 15 an inner liner 16 is arranged. By its walls the inner liner 16 bounds a receiving space 17 for food. The receiving space 17 may be a cooling compartment. The household cooling appliance 14 moreover comprises a door 18. The door 18 is configured for front side closure of the receiving space 17. It is movably arranged on the housing 15. FIG. 4 shows in an exemplary way that a storage container 1 is arranged in the receiving space 17. The storage container 1 may be configured according to an embodiment as it was explained in connection with FIG. 1.

It is also possible that the household cooling appliance 14 comprises an evaluation unit 6, 6', which is arranged external to the storage container 1. The same additionally or instead may also be envisaged for instance for the output unit 8, 8' and/or the input unit 9, 9'.

In one further embodiment the household cooling appliance 14 may be integral part of the communication network 11. Then also an evaluation unit 6, 6' can be arranged external to the household cooling appliance 14.

For instance, in another embodiment the evaluation unit 8 or 8', respectively, and/or the input unit 9 or 9', respectively, may be integral part of a portable communication terminal device. Such a communication terminal device may be a mobile radio terminal device or a tablet.

In FIG. 4 also the backend 12 is shown in an exemplary way. This may be present if a communication network 11 is formed and the household cooling appliance 14 is integral part of this communication network 11.

Figure 3:
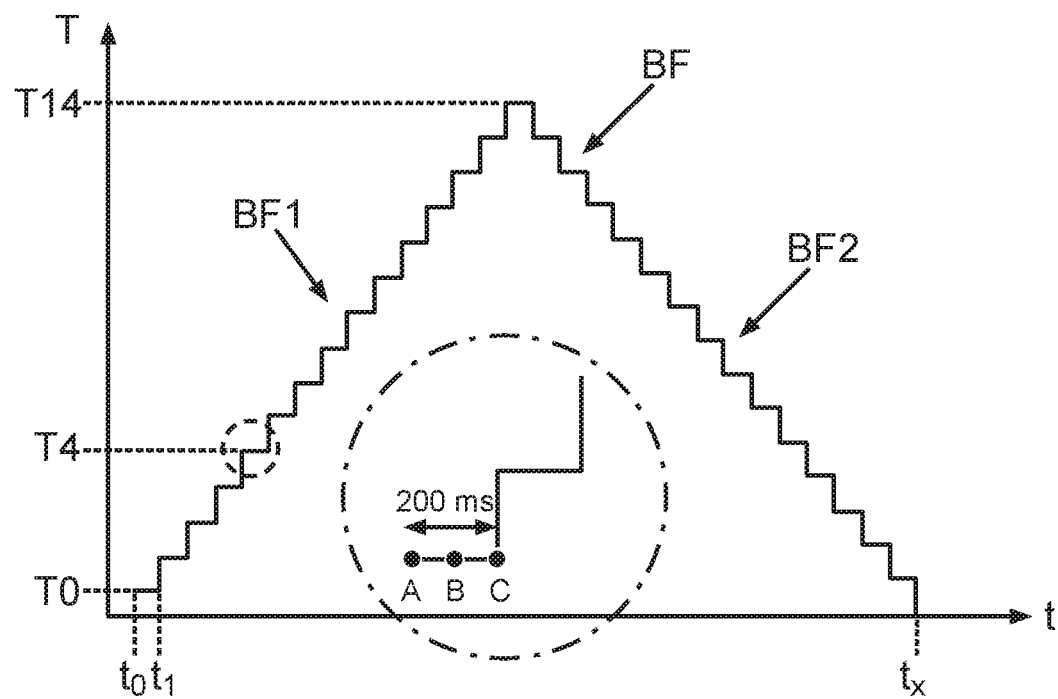
FIG. 3 an embodiment of a simplified diagram for the operating temperatures of a MOX sensor for determining the freshness state of a food in a storage container.

In FIG. 3, in an embodiment, a diagram is shown in which the time t is plotted on the horizontal axis and the temperature T on the vertical axis. As embodied here, an operating temperature function BF is shown. This is an embodiment as to how a dynamic operating mode of the MOX sensor 5 is performed during a freshness state determination cycle. Here it can be recognized that this operating temperature function BF is a stepped function. In the embodiment, it comprises an ascending branch BF1. Moreover, in an embodiment, it also comprises a descending branch BF2. In an embodiment, starting from the point in time t0 the operation of the MOX sensor 5 is started during a freshness state determination cycle. Then the operating temperature T0 is set in a defined way. In this dynamic operation mode, the same is set and maintained for a predetermined period of time, which is measured between the points in time t0 and t1. During this period of time, between the points in time t0 and t1 at least one measurement or a capturing operation is performed by the MOX sensor 5 on the gas mixture. In at least some, in particular all, different operating temperatures, as they are predetermined by this stepped profile, in each case several measuring or capturing operations are performed on the gas mixture. In FIG. 3, in this regard exemplarily in one place of this stepped function for a temperature an enlarged view is shown. Here this relates exemplarily to the temperature T4. It is to be recognized that this operating temperature T4 is set for a period of time of here for instance 200 ms. In this time interval here exemplarily three separate measuring or capturing operations A, B, and C are performed by the MOX sensor 5.

It is also possible that at all set operating temperatures in each case an identical number of capturing or measuring operations are performed. It may, however, also be envisaged that this number of measuring operations varies depending on the respective set operating temperature T.

In FIG. 3 a duration of a freshness state determination cycle is exemplarily represented. This duration is measured between the point in time t0 and the point in time tx.

Immediately subsequent to the point in time tx then a second freshness state determination cycle may be effected. However, also a certain duration of a pause after the point in time tx may follow and only after this pause then an at least second freshness state determination cycle be performed.

By this very setting of different operating temperatures, in particular a stepped profile, as it is shown in FIG. 3, a sensitivity and a selectivity of the MOX sensor 5 can be clearly raised. The individual molecules at these different temperatures respond in this regard individually so that the analysis of the entire gas mixture is basically only facilitated by this dynamic operating mode of the MOX sensor 5 and moreover can be effected very precisely, too. This has crucial advantages over common MOX sensors, which can be operated only at one operating temperature and thus also are sensitive only to a specific molecule.

Commonly in such gas mixture also other molecules, such as ketones and alcohol, are present. Moreover, also the humidity and the temperature in the storage container play an influential role and sensors for measurement these magnitudes could also be added and used for an improved detection.

Preferably, the operating temperature of the MOX sensor 5 in discrete temperature steps explained in this regard can be changed in a value interval of for instance 130° C. to 350° C. In particular, the temperature range between 130° C. and 200° C. is advantageous for the dominant molecule ester.

It is also possible that the MOX sensor 5 provides a plurality of values at different points in time and different operating temperatures. This may be up to 180 values. These values in sum represent a data point. These up to preferably 180 values are used as a basis for the state determination of the gas mixture and depending thereon in turn for the determination of the freshness state of the food and are regarded as a data point.

Figure 5:
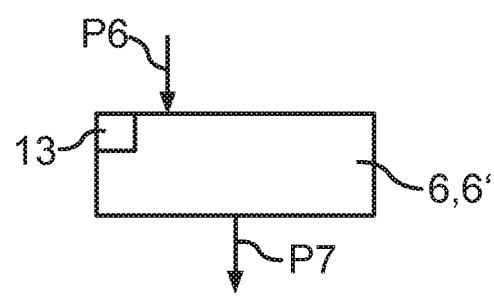
FIG. 5 a schematic view of an evaluation unit, by which in an embodiment a method for determining an electronic future information for a food is performed.

In FIG. 5, a simplified representation of an evaluation unit 6 or 6' is shown respectively. By this evaluation unit 6 or 6' also a method, in particular a computer-implemented method, for generating an information relating to a food can be performed. Thus a method for operating a food keep-fresh system can be performed.

In an embodiment according to arrow P6 an electronic information, in particular an additional information, relating to a freshness state of a food 2 in a storage container 1 can be provided to the evaluation unit 6 or 6', respectively, in particular be received by the evaluation unit 6, 6'. This electronic information in an embodiment can be generated on the basis of the above-named method for determining such freshness state of a food 2. Here, too, this determined freshness is an electronic information relating to this freshness state.

Based on this provided electronic information an electronic future information relating to the food 2 is generated by the evaluation unit 6 or 6', respectively. This at least one electronic future information according to the arrow P7 is provided by the evaluation unit 6 or 6', respectively. This generated electronic future information P7 is output by the evaluation unit 6 or 6', respectively.

In an embodiment an electronic future information may comprise a consumption sequence in which food 2 in the storage container 1 is to be consumed. In particular this is advantageous if in the storage container 1 several different kinds of food are contained or several separate portions of the same food 2 are stored therein. Thus, also a priority list for the consumption of this stored food can be effected by the evaluation unit 6, 6'.

It is possible in a further embodiment that as an electronic future information a prediction information is generated. In this prediction, the future freshness state of the future freshness state change of the food 2 is predicted or estimated. In this context, critical changes in the freshness state, if given, can also be temporally predicted.

In an embodiment as an electronic future information a storage information can be generated, by which storage conditions for the food are suggested for the future. This may for instance concern parameters which relate to the humidity and/or the temperature in the storage container 1 and are to be set in the future.

In a further embodiment as an electronic future information a reminder information can be generated, by which a reminder is generated that the food 2 is stored in the storage container 1. It is not uncommon for a user to forget that he has food 2 stored in the storage container 1. Unknowingly, thus, the freshness state of the food 2 changes to the effect that, if applicable, a consumption is only possible to a limited extent or no longer possible at all.

In a further embodiment an electronic future information may comprise a preparation information, by which a preparation suggestion for a consumption of the food 2 is generated. For instance, in this context, various recipes for the preparation of the food 2 may be suggested.

In an embodiment a future information may be generated based on current information of the food 2 and/or based on past information relating to the food 2. For instance, here also past use behavior of a user can be considered. In particular with regard to the various examples, as they were named for electronic future information and as they were suggested in this regard in the past for a corresponding food 2 or for other food, may here be considered. In particular, as to whether corresponding presented future information generated in the past were then correspondingly executed by a user. Thus, also a use and an acceptance of this generated electronic future information can be assessed in a self-learning manner. In particular, also a priority list for corresponding different future information can be established. In this context, it is also possible that depending on the respective food 2 to be assessed it is recognized which electronic future information generated in the past was more or less executed or utilized by a user and which were not. Thus, the system even then, depending on the respective food 2 to be currently evaluated, can generate an electronic future information more in line with demand and/or generate an accordingly better adapted priority list of the electronic future information.

In an embodiment the computer program product may also be a software application. The same may be installed in the evaluation unit 6, 6'. It may also be installed for instance on a portable communication terminal device.

In an embodiment the at least one electronic future information generated and provided by the evaluation unit 6 or 6', respectively, is output at an output unit. The output unit may for instance be the output unit 8 or 8', respectively. As already explained with regard to FIG. 4, such an output unit 8 or 8', respectively, may also be arranged on an outer face of the door 18 of the household cooling appliance 14.

The following is a summary list of reference numerals and the corresponding structure used in the above description of the invention:

LIST OF REFERENCE SIGNS 1 storage container
2 food
3 storage bowl
4 cover
5 MOX sensor
6 evaluation unit
6' evaluation unit
7 food keep-fresh system
8 output unit
8' output unit
9 input unit
9' input unit
10 optical capturing unit
11 communication network
12 backend
13 computer program product
14 household cooling appliance
15 housing
16 inner liner
17 receiving space
18 door
t time
t0 point in time
tx point in time
A capturing
B capturing
C capturing
BF operating temperature function
BF1 ascending branch
BF descending branch
P1 arrow
P2 arrow
P3 arrow
P4 arrow
P5 arrow
P6 arrow
P7 arrow
T temperature
T0 operating temperature
T4 operating temperature

The invention claimed is:

1. A method, for determining a freshness state of a food in a storage container, the method comprising:
  performing a first freshness state determination cycle of the food by,
    setting a first operating temperature of at least one MOX sensor, and capturing a gas mixture in the storage container by the MOX sensor at the first operating temperature;
    setting at least one second operating temperature of the MOX sensor that is different from the first operating temperature, and capturing a gas mixture in the storage container by the MOX sensor at the second operating temperature;
  determining, by an evaluation unit, a state of the gas mixture based on the information captured at the at least two operating temperatures during the first freshness state determination cycle;
  performing a second freshness state determination cycle of the food temporally consecutively to the first freshness state determination cycle, in the second freshness state determination cycle,
    setting the first operating temperature of the MOX sensor, and capturing a gas mixture in the storage container by the MOX sensor at this first operating temperature;
    setting at least the second operating temperature of the MOX sensor that is different from the first operating temperature, and capturing a gas mixture in the storage container by the MOX sensor at the second operating temperature;
  determining, by the evaluation unit, a state of the gas mixture based on the information captured at the two operating temperatures during the second freshness state determination cycle;
  determining, by the evaluation unit, the freshness state of the food in the storage container based on the state of the gas mixture that was determined in the first freshness state determination cycle and based on the state of the gas mixture which was determined in the at least second freshness state determination cycle;
  the step of determining the freshness state of the food in the storage container further including the steps of:
    analyzing captured information of the MOX sensor as actual signal sequences, and
    comparing the actual signal sequences with reference signal sequences; and
  the reference signal sequences being machine trained in a preprocessing phase of the method using machine learning, the machine training using the determined freshness state to update at least one of the reference signal sequences and/or a freshness state class maintained by the system.

2. The method according to claim 1, further comprising:
  capturing at least one characteristic feature of the gas mixture in the first freshness state determination cycle at least at one of the operating temperatures of the MOX sensor at least at two different points in time; and/or capturing at least one further characteristic feature of the gas mixture in the second freshness state determination cycle at least at one of the operating temperatures of the MOX sensor at least at two different points in time.

3. The method according to claim 1, wherein at least one operating temperature is set in at least one of the freshness state determination cycles for a time period of between 150 ms and 250 ms.

4. The method according to claim 2, wherein a state of the gas mixture is determined by, measuring a composition of the gas mixture at the respective points in time at which the operating temperatures were set in the respective freshness state determination cycle; and
  analyzing a change in the composition of the gas mixture from one freshness state determination cycle to another freshness state determination cycle.

5. The method according to claim 1, wherein specific freshness states of the food are characterized by the reference signal sequences.

6. The method according to claim 5, the method further comprising:
  defining freshness state classes of the food by the reference signal sequences; and
  classifying current freshness state of a food into a freshness state class depending on the outcome of the comparing of the actual signal sequences with the reference signal sequences.

7. The method according to claim 6, wherein:
  at least a first freshness state class is predetermined in which the food is free of mold;
  at least a second freshness state class is predetermined in which the food has developed mold; and
  during the step of determining the freshness state of the food, characterizing, by the evaluation unit, a probability relationship between the assignment of the determined freshness state and a freshness state class.

8. The method according to claim 1, wherein the determining of the freshness state of the food in the storage container is at least partially performed by machine training.

9. The method according to claim 1, the method further comprises outputting, through an output unit, the determined freshness state of food, where the output unit is an optical unit which displays a symbol corresponding to the determined freshness state.

10. The method according to claim 1, the method further comprises outputting, through an output unit, the determined freshness state of food, where the output unit is an acoustic unit which generates a sound corresponding to the determined freshness state.

11. The method according to claim 1, the method further comprises outputting, through an output unit, the determined freshness state of food, where the output unit is a display unit of a smart device which displays a symbol or generates a sound corresponding to the determined freshness state.

12. The method according to claim 1, wherein in a performing at least the first freshness state determination cycle, a temperature profile for the operating temperature is predetermined, which is an ascending and/or descending stepped profile so that temporally consecutively at more than two operating temperatures the gas mixture is captured in each case at least once by the MOX sensor.

13. The method according to claim 1, wherein the freshness state determination cycles are performed without capturing pause immediately consecutively.

14. The method according to claim 1, wherein a capturing pause is performed between the at least two freshness state determination cycles.

15. A non-transitory computer program product comprising instructions, which upon the execution of the program by a computer, the computer performs the method according to claim 1.

16. A storage container for food, comprising:
  a storage bowl configured for storing food;
  a MOX sensor; and
  an evaluation unit;
  said storage container configured to perform the method according to claim 1.

* * * * *